(12) United States Patent
Miyoshi

(10) Patent No.: US 8,716,174 B2
(45) Date of Patent: May 6, 2014

(54) METHOD FOR PRODUCING FINE METAL HYDROXIDE PARTICLES

(75) Inventor: Yoshiyuki Miyoshi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 633 days.

(21) Appl. No.: 13/051,422

(22) Filed: Mar. 18, 2011

(65) Prior Publication Data

US 2011/0230673 A1 Sep. 22, 2011

(30) Foreign Application Priority Data

Mar. 19, 2010 (JP) ................................ 2010-064387

(51) Int. Cl.
*B01J 21/10* (2006.01)

(52) U.S. Cl.
USPC ............................ 502/340; 502/300; 568/851

(58) Field of Classification Search
USPC .................................. 568/851; 502/340, 300
See application file for complete search history.

(56) References Cited

U.S. PATENT DOCUMENTS

2006/0128865 A1    6/2006    Kodama et al.

FOREIGN PATENT DOCUMENTS

| JP | 2002-348574 A | 12/2002 |
|----|---------------|---------|
| JP | 2005-288254 A | 10/2005 |
| JP | 2005330343 A  | 12/2005 |
| JP | 4339163 B2    | 7/2009  |
| WO | 2004065300 A1 | 8/2004  |

OTHER PUBLICATIONS

Rodorico Giorgi, et al, "Nanoparticles of Mg(OH): Synthesis and Application to Paper Conservation", Langmuir, Aug. 6, 2005, pp. 8495-8501, vol. 21 (18).
Notification of Reasons for Rejection, dated Jul. 30, 2013, issued in corresponding JP Application No. 2010-064387, 7 pages in English and Japanese.

*Primary Examiner* — Elvis O Price
(74) *Attorney, Agent, or Firm* — Sughrue Mion, PLLC

(57) ABSTRACT

There is provided a production method in which highly transparent fine metal hydroxide particles having a small particle size and excellent in monodispersibility can be easily produced without requiring grinding. The method for producing fine metal hydroxide particles at least includes: a reaction step of mixing an aqueous solution of a metal salt, for example, a magnesium salt, with an aqueous solution of a hydroxide salt to precipitate metal hydroxide particles in an uncrystallized state; a purification step of removing by-product salt from a mixed solution containing the precipitated metal hydroxide particles in an uncrystallized state; a surface treatment step of treating the metal hydroxide particles in an uncrystallized state obtained through the purification step with a surface-treatment agent on the surface thereof; and a heating step of crystallizing the surface-treated metal hydroxide particles in an uncrystallized state by hydrothermal treatment.

14 Claims, 10 Drawing Sheets

METHOD FOR PRODUCING FINE METAL HYDROXIDE PARTICLES

BACKGROUND OF THE INVENTION

1. Field of the Invention

The present invention relates to a method for producing fine metal hydroxide particles, particularly to a method for producing fine magnesium hydroxide particles.

2. Description of the Related Art

Hithertofore, polymeric materials and thermoplastic resins have been used in various fields as materials for electrical and electronic equipment parts, housings, and the like. When polymeric materials are used as covering materials of OA equipment such as television sets and personal computers, the polymeric materials are required to have flame retardancy from the viewpoint of safety.

As a method for imparting flame retardancy to a polymeric material, a flame retardant is added to the polymeric material. Typical flame retardants include those based on halogen, phosphorus, and inorganic particles. However, halogen flame retardants have many problems in an environmental aspect such as generation of halogen gas and black smoke during combustion and generation of dioxin during incineration. Further, phosphorus flame retardants also have problems in an environmental aspect such as generation of phosphine gas, and in addition, they have a problem such as high cost and concern about the supply of phosphate rock which is a raw material.

On the other hand, metal hydroxides representing inorganic particle flame retardants such as fine magnesium hydroxide particles are harmless and have few problems in an environmental aspect. The metal hydroxides further have features such as low cost and abundant raw material resources and can solve the problems of both halogen flame retardants and phosphorus flame retardants.

For example, Japanese Patent Application Laid-Open No. 2002-348574 discloses a method for producing magnesium hydroxide particles including producing a coprecipitate of magnesium hydroxide by neutralization, producing fine magnesium hydroxide particles by hydrothermal reaction, and surface-treating the fine magnesium hydroxide particles, followed by filtrating, water washing, drying, and grinding.

SUMMARY OF THE INVENTION

The method of Japanese Patent Application Laid-Open No. 2002-348574 includes hydrothermal reaction after producing a coprecipitate of magnesium hydroxide particles. When a coprecipitate is produced, a salt is produced as a by-product. The presence of the by-product salt will cause aggregation and precipitation of magnesium hydroxide particles during hydrothermal reaction due to the effect of the salting out of the by-product salt. Therefore, in order to produce magnesium hydroxide particles, a grinding step is needed after the hydrothermal reaction. The grinding step for dispersion requires high dispersion energy. Impurities are liable to be incorporated into fine magnesium hydroxide particles by performing the grinding step.

The present invention has been made in view of such circumstances, and an object of the present invention is to provide a method for producing fine metal hydroxide particles which are less liable to cause aggregation and precipitation without requiring grinding.

According to one aspect of the present invention, there is provided a method for producing fine metal hydroxide particles, comprising: a reaction step of mixing an aqueous solution of a metal salt with an aqueous solution of a hydroxide salt to precipitate metal hydroxide particles in an uncrystallized state; a purification step of removing by-product salt from a mixed solution containing the precipitated metal hydroxide particles in an uncrystallized state; a surface treatment step of treating a surface of the metal hydroxide particles in an uncrystallized state obtained through the purification step with a surface-treatment agent; and a heating step of crystallizing the surface-treated metal hydroxide particles in an uncrystallized state by hydrothermal treatment.

Since the by-product salt causing the salting out has been removed after the reaction step, the metal hydroxide particles can be prevented from aggregation and precipitation. Further, since the metal hydroxide particles has been subjected to surface treatment after the purification step, the surface of the metal hydroxide particles can be stabilized. Thereby, the metal hydroxide particles can be prevented from aggregation and growth during hydrothermal treatment.

According to another aspect of the present invention, the metal salt is preferably a magnesium salt.

According to another aspect of the present invention, it is preferred that the concentration of the by-product salt after the purification step be 0.05% or less, preferably 0.01% or less. The aggregation and precipitation of the metal hydroxide particles can be more positively prevented by reducing the concentration of the by-product salt to the above-mentioned range.

According to another aspect of the present invention, the reaction step preferably comprises supplying the aqueous solution of the metal salt through some of a plurality of supply channels of a microdevice having a plurality of supply channels for supplying two or more fluids, a junction joined to the plurality of supply channels, and a discharge channel connected to the junction, supplying the aqueous solution of the hydroxide salt through others of the plurality of supply channels, mixing the metal salt with the hydroxide salt in the junction, and discharging a mixed solution from the discharge channel.

Fine metal hydroxide particles having a small particle size and excellent in monodispersibility can be obtained by using a micro-device.

According to another aspect of the present invention, the surface-treatment agent is preferably a silane coupling agent because various functional groups can be selected for the silane coupling agent.

According to another aspect of the present invention, the silane coupling agent is preferably in the range of 0.1 to 50% by weight based on the metal hydroxide particles, in the surface treatment step.

If the amount of the silane coupling agent added is less than 0.1% by weight, the surface stability of the particles will be extremely reduced to promote the aggregation and growth in the heating step. As a result, the particles having a desirable particle size and degree of dispersion may not be obtained. Further, if the amount of the silane coupling agent added exceeds 50% by weight, excessive silane coupling agent molecules which do not contribute to the reaction with the surface will increase. If the heating step is performed in the presence of the excessive molecules, the excessive molecules will aggregate to each other to cause aggregation of the particles via the resulting aggregates. Therefore, the heating in the presence of excessive molecules is not preferred.

According to another aspect of the present invention, the heating step is preferably followed by a drying step. Drying can facilitate the reduction in transportation cost and the change of a dispersion medium.

According to another aspect of the present invention, the crystallized metal hydroxide particles preferably have a volume average particle size (MV) of 0.01 µm to 1 µm and a ratio (MV/MN) of the volume average particle size (MV) to the number average particle size (MN) of 2.0 or less. The fine metal hydroxide particles can have very high transparency and excellent flame retardancy by setting the volume average particle size and the ratio of the volume average particle size (MV) to the number average particle size (MN) to be in the above-mentioned ranges.

According to the present invention, highly transparent fine metal hydroxide particles having a small particle size and excellent in monodispersibility can be easily produced without requiring grinding.

DETAILED DESCRIPTION OF THE PREFERRED EMBODIMENTS

Hereinafter, preferred embodiments of the present invention will be described with reference to accompanying drawings. Although the present invention will be described by the following preferred embodiments, it can be modified by a large number of methods without departing from the scope of the present invention, and other embodiments other than the present embodiment can also be used. Accordingly, all the modifications within the scope of the present invention are included in the claims. Furthermore, the numerical value range represented by using "to" in the present specification means the range including the numerical values described before and after the "to".

The embodiments will be described below using a method for producing fine magnesium hydroxide particles as an example.

Figure 1:
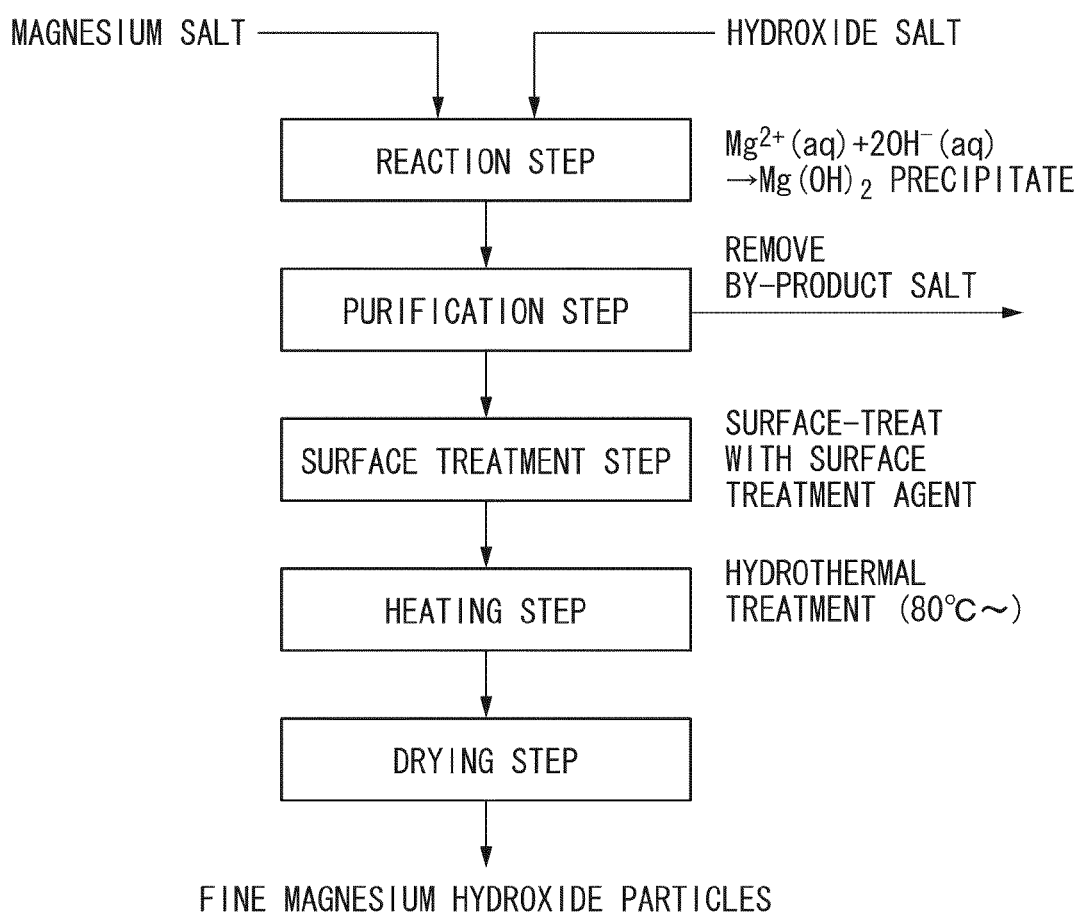
FIG. 1 is a schematic diagram showing an example of a flow of a method for producing fine metal hydroxide particles according to the present invention.

FIG. 1 shows a production flow of the present embodiment. First, in a reaction step, a magnesium salt is mixed with a hydroxide salt to precipitate magnesium hydroxide particles in an uncrystallized state. Next, in a purification step, a salt which is a by-product is removed from a mixed solution from which the magnesium hydroxide particles are precipitated. This suppresses the aggregation and precipitation of the magnesium hydroxide particles by salting out. Next, in a surface treatment step, the surface of the magnesium hydroxide particles is treated with a surface-treatment agent. This can stabilize the surface of the magnesium hydroxide particles. Next, in a heating step, the magnesium hydroxide particles in an uncrystallized state are crystallized by hydrothermal treatment. Since the surface of the magnesium hydroxide particles has been subjected to surface treatment, magnesium hydroxide particles do not aggregate and grow during the hydrothermal treatment. Finally, the heat treatment may optionally be followed by a drying step. Drying facilitates reduction in the cost of transporting magnesium hydroxide particles and the change of a dispersion medium.

Next, each step will be described in more detail.

<Reaction Step>

A magnesium salt such as magnesium chloride ($MgCl_2$) and a hydroxide salt such as sodium hydroxide (NaOH) are previously dissolved in a solvent, respectively. An aqueous solution of a magnesium salt is mixed with an aqueous solution of a hydroxide salt to precipitate magnesium hydroxide particles.

Figure 2:
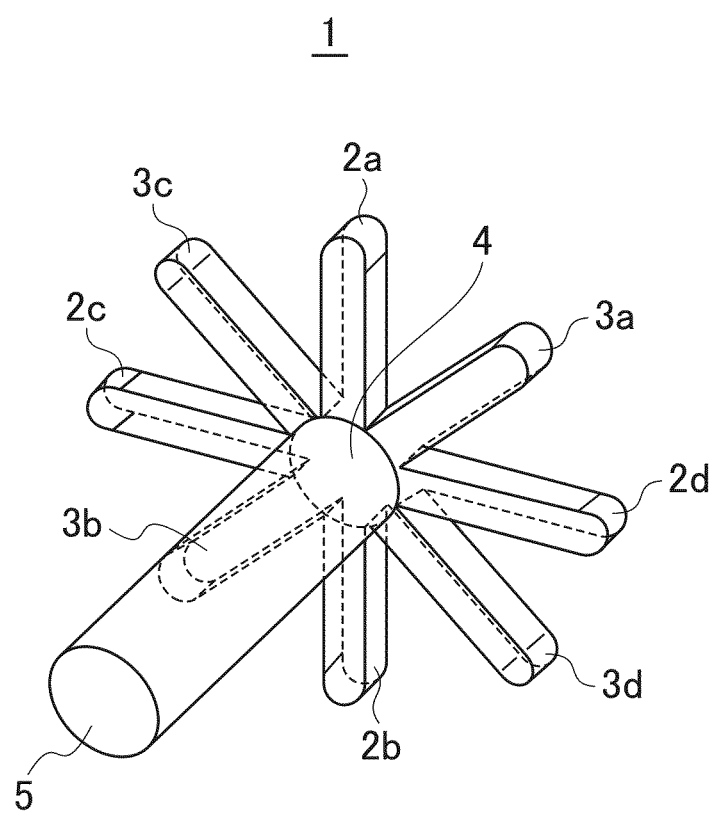
FIG. 2 is a schematic diagram showing a structure of a micro-device.

In the reaction step, the mixing and precipitation can be implemented, for example, using a micro-device as described in Japanese Patent No. 4339163. FIG. 2 is a schematic diagram showing the structure of the micro-device. The micro-device 1 has a plurality of supply channels 2 (2a, 2b, 2c, 2d) and 3 (3a, 3b, 3c, 3d) which can supply two or more fluids, a junction 4 connected to the plurality of supply channels 2 and 3 for mixing the fluids from the plurality of supply channels 2 and 3, and a discharge channel 5 connected to the junction 4 for discharging a mixed fluid out of the junction 4.

A reaction using the micro-device shown in FIG. 2 will be described. A magnesium chloride solution is introduced into the supply channels 2a, 2b, 2c and 2d which supply one type of fluid. A sodium hydroxide solution is introduced into the supply channels 3a, 3b, 3c, and 3d which supply another type of fluid. The magnesium chloride solution is mixed with the sodium hydroxide solution at the junction 4. Then, the mixed solution that has been mixed at the junction 4 is discharged to the discharge channel 5. The reaction progresses within the discharge channel 5 and the precipitation of magnesium hydroxide starts. Particularly, a flow field in one direction can be achieved within the discharge channel 5 by using the micro-device 1 shown in FIG. 2. Thereby, the aggregation is suppressed.

Note that in the present embodiment, the micro-device shown in FIG. 2 has been used as an example of a micro-device. The micro-device used in the present embodiment is not at all limited to a specific structure.

In the present embodiment, magnesium chloride ($MgCl_2$) has been used as a magnesium salt. For example, magnesium nitrate ($Mg(NO_3)_2$), magnesium sulfate ($Mg(SO_4)$), and the like can also be used as a magnesium salt to be used in the present embodiment.

In the present embodiment, sodium hydroxide (NaOH) has been used as a hydroxide salt. Potassium hydroxide (KOH), calcium hydroxide ($Ca(OH)_2$), ammonium hydroxide ($NH_4OH$), and the like can also be used as a hydroxide salt to be used in the present embodiment.

<Purification Step>

A salt which is a by-product generated in the reaction (sodium chloride (NaCl) in the above-mentioned reaction) is removed. The magnesium hydroxide particles which precipitate in the reaction step essentially have self-dispersibility. However, if a by-product salt is present, the magnesium hydroxide particles will start to aggregate and precipitate due to the salting out effect of the by-product salt. By purifying immediately after the reaction to remove the by-product salt, the magnesium hydroxide particles are disaggregated and easily dispersed in a solvent with the original self-dispersibility thereof.

As a method of purification, there can be employed a filtering method utilizing a membrane, a precipitation method utilizing centrifugal force, an electrodialysis method utilizing electrostatic force, and the like. In the purification step, the by-product salt is preferably removed to a concentration of 0.05% or less, more preferably 0.01% or less. The concentration of the by-product salt in this range can suppress aggregation and precipitation of the magnesium hydroxide particles.

<Surface Treatment Step>

The surface of the fine magnesium hydroxide particles after purification is treated with at least one surface-treatment agent selected from higher fatty acids, higher fatty acid alkali metal salts, polyhydric alcohol higher fatty acid esters, anionic surfactants, phosphoric esters, silane coupling agents, aluminum coupling agents, titanate coupling agents, organosilanes, organosiloxanes, and the organosilazanes. The application of surface treatment can stabilize the surface of the fine magnesium hydroxide particles.

From the viewpoint of the adhesiveness between the treatment agent and particles, a silane coupling agent, an aluminum coupling agent, and a titanate coupling agent are preferably used as a surface-treatment agent. Particularly, it is preferred to use a silane coupling agent since various functional groups can be selected.

The surface-treatment agent is applied in the range of 0.1 to 50% by weight, preferably in the range of 0.5 to 30% by weight, more preferably in the range of 2 to 20% by weight based on the fine magnesium hydroxide particles.

If the amount of the silane coupling agent added is less than 0.1% by weight, the surface stability of the particles will be extremely reduced to promote the aggregation and growth in the heating step. As a result, the particles having a desirable particle size and degree of dispersion may not be obtained. Further, if the amount of the silane coupling agent added exceeds 50% by weight, excessive silane coupling agent molecules which do not contribute to the reaction with the surface will increase. If the heating step is performed in the presence of the excessive molecules, the excessive molecules will aggregate to each other to cause aggregation of the particles via the resulting aggregates. Therefore, the heating in the presence of excessive molecules is not preferred.

<Heating Step>

The surface-treated magnesium hydroxide particles are subjected to hydrothermal treatment to promote crystallization of the magnesium hydroxide particles. This flattens the magnesium hydroxide particles to increase the specific surface area thereof.

When the specific surface area of the magnesium hydroxide particles is increased, improvement in the flame retardancy of the magnesium hydroxide particles can be expected when they are used as a flame retardant.

Specifically, the surface-treated magnesium hydroxide particles are subjected to hydrothermal treatment in an autoclave at 120° C. or higher for 8 hours or more. The hydrothermal treatment is preferably performed at least at 80° C. or higher for 8 hours or more.

According to the method of the present embodiment, magnesium hydroxide particles can be produced without giving high dispersion energy such as high pressure and high shear. Furthermore, the magnesium hydroxide particles can be easily taken out since the particles are fine and individually dispersed in a solvent without aggregation.

The magnesium hydroxide particles produced by the method of the present embodiment is featured to have a volume average particle size (MV) in the range of 0.01 to 1 μm and a ratio (MV/MN) of the volume average particle size (MV) to the number average particle size (MN) of 2.0 or less.

<Drying Step>

A general drying method can be used as a drying step. Specifically, the fine metal hydroxide particles can be dried by using a method such as a heat-drying method, a vacuum drying method, centrifugal drying, a spray drying method, and a freeze drying method. In particular, the surface tension of a solvent during drying can be suppressed by using a freeze drying method in which the solvent and the particles can be separated by sublimation during drying. As a result, redispersibility can be improved.

EXAMPLES

Hereinafter, the present invention will be more specifically described with reference to Examples. Appropriate modifications can be made to the materials, the amount used, the proportion, the contents of treatment, the procedures of treatment, and the like as described in the following Examples so long as they do not depart from the spirit of the present invention. Accordingly, the scope of the present invention is not limited to the specific examples to be described below.

Example 1

Figure 3A:
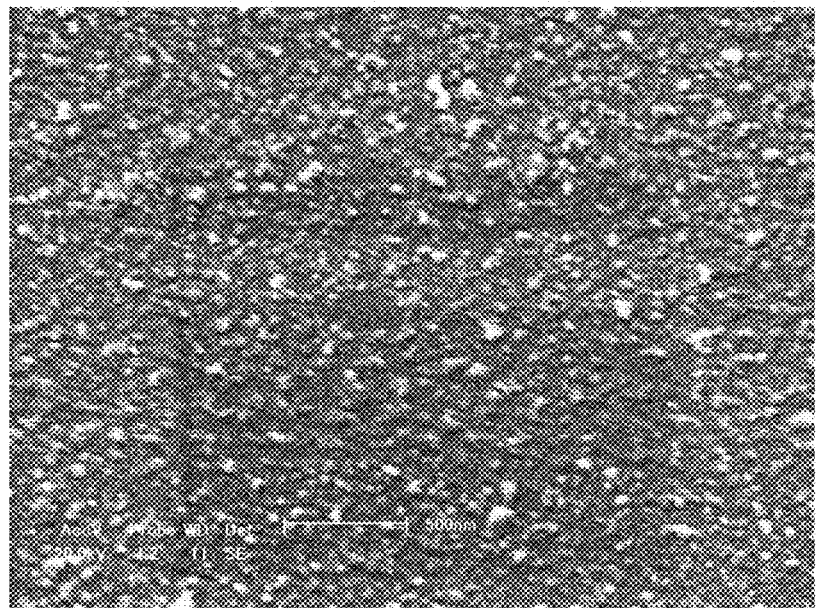
FIG. 3A shows a SEM image of magnesium hydroxide obtained in Example 1.
Figure 3B:
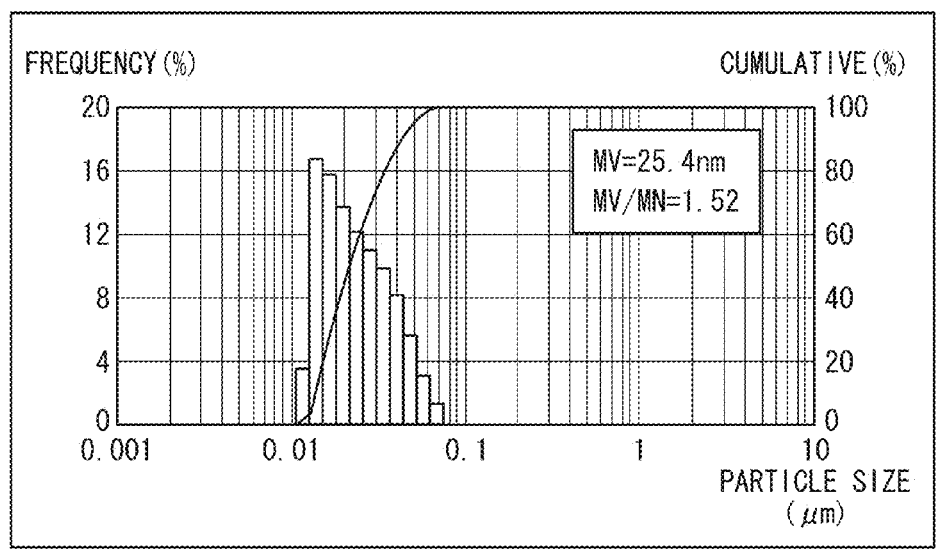
FIG. 3B shows particle size distribution data of the aqueous dispersion obtained in Example 1.

There were prepared an aqueous magnesium chloride solution adjusted to 1 mol/L and an aqueous sodium hydroxide solution adjusted to 6 mol/L. The aqueous solutions were mixed with each other in a flow rate ratio of 200 cc/min ($MgCl_2$) to 100 cc/min (NaOH) in a micro-device at a temperature of 90° C. to obtain a magnesium hydroxide slurry. The resulting slurry was purified by water washing until the salt concentration reaches 0.00% to obtain an aqueous dispersion of fine magnesium hydroxide particles without aggregation. To the resulting aqueous dispersion was added 3-aminopropyltrimethoxysilane in an amount of 10% by weight based on the magnesium hydroxide particles, and the resulting mixture was kept at a room temperature of 20 to 25° C. for 30 minutes with stirring to surface-treat the particles. Then, the aqueous dispersion was further heated at 120° C. for 2 hours with stirring, and dried. FIG. 3A shows a SEM image of magnesium hydroxide obtained in Example 1, and FIG. 3B shows particle size distribution data of the aqueous dispersion obtained in Example 1.

Example 2

Figure 4A:
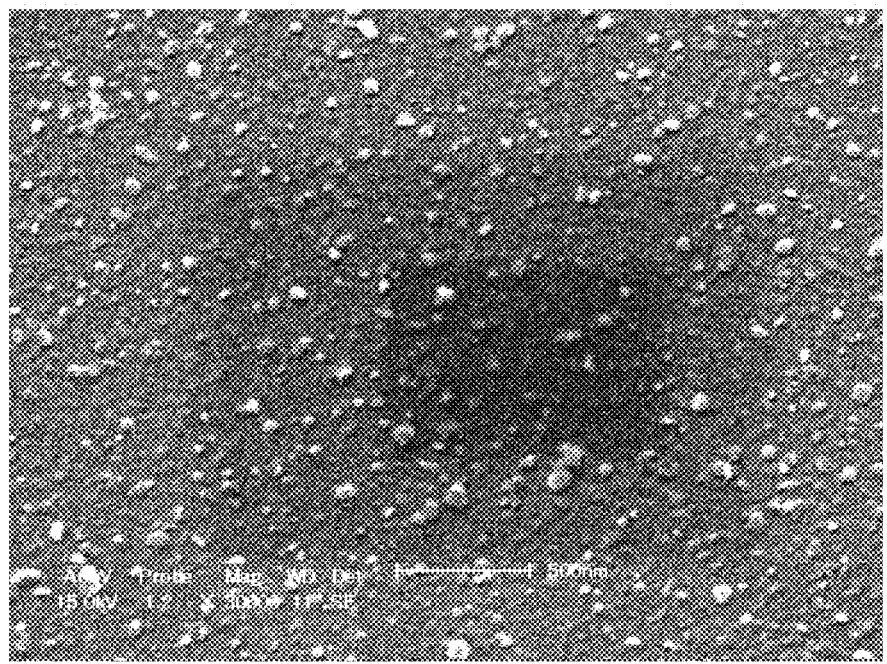
FIG. 4A shows a SEM image of magnesium hydroxide obtained in Example 2.
Figure 4B:
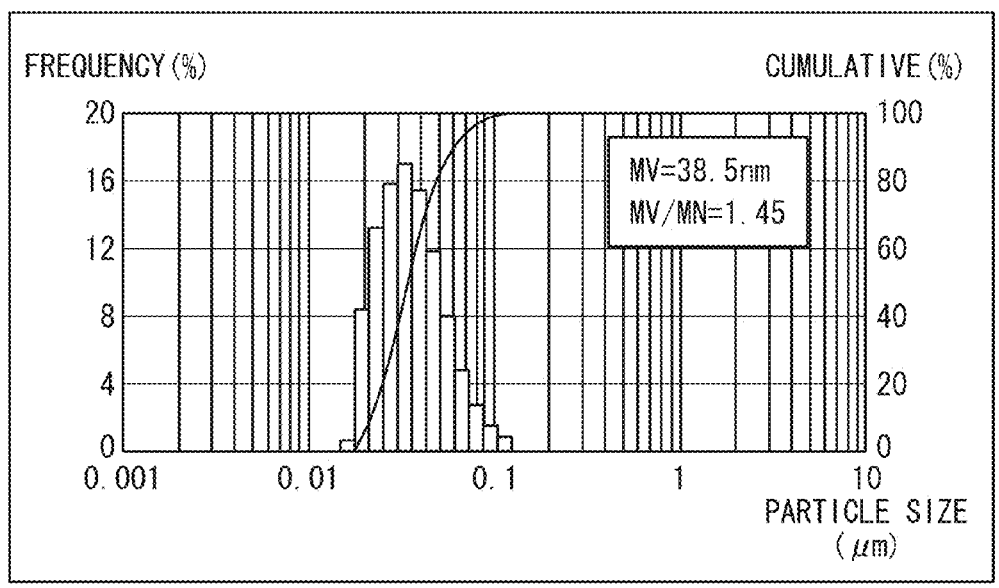
FIG. 4B shows particle size distribution data of the aqueous dispersion obtained in Example 2.

There were prepared an aqueous magnesium chloride solution adjusted to 1 mol/L and an aqueous sodium hydroxide solution adjusted to 6 mol/L. The aqueous solutions were mixed with each other in a flow rate ratio of 200 cc/min (MgCl$_2$) to 100 cc/min (NaOH) in a micro-device at a room temperature of 20 to 25° C. to obtain a magnesium hydroxide slurry. The resulting slurry was purified by water washing until the salt concentration reaches 0.00% to obtain an aqueous dispersion of fine magnesium hydroxide particles without aggregation. To the resulting aqueous dispersion was added 3-aminopropyltrimethoxysilane in an amount of 10% by weight based on the magnesium hydroxide particles, and the resulting mixture was kept at a room temperature of 20 to 25° C. for 30 minutes with stirring to surface-treat the particles. Then, the aqueous dispersion was further heated at 120° C. for 2 hours with stirring, and dried. FIG. 4A shows a SEM image of magnesium hydroxide obtained in Example 2, and FIG. 4B shows particle size distribution data of the aqueous dispersion obtained in Example 2.

Example 3

Figure 5A:
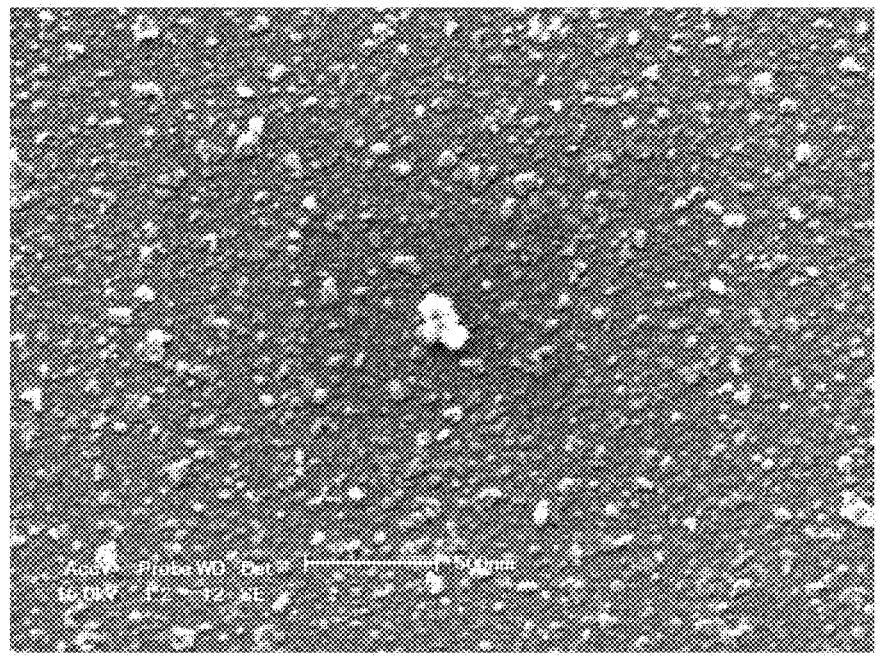
FIG. 5A shows a SEM image of magnesium hydroxide obtained in Example 3.
Figure 5B:
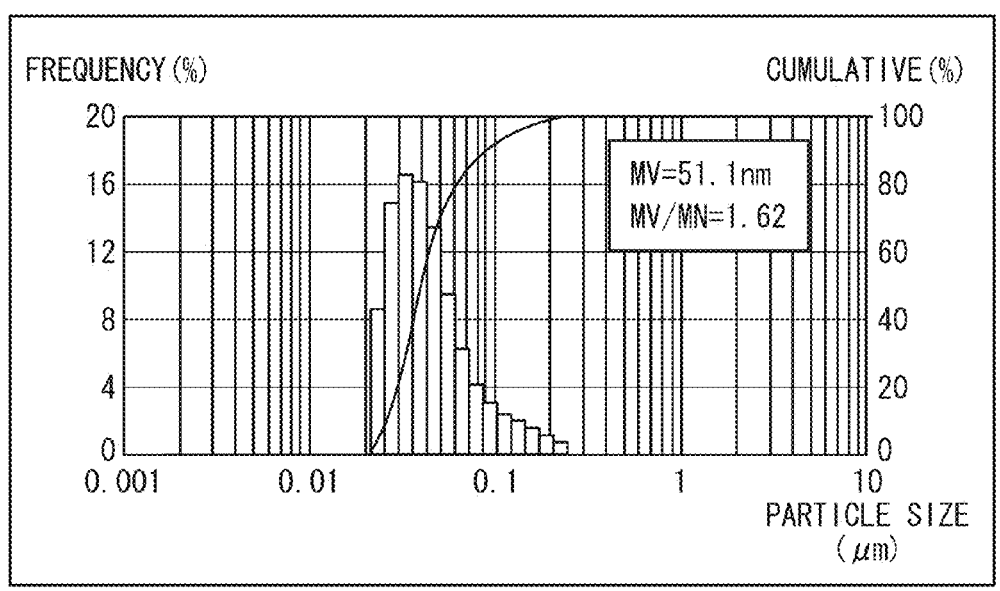
FIG. 5B shows particle size distribution data of the aqueous dispersion obtained in Example 3.

There were prepared an aqueous magnesium chloride solution adjusted to 0.5 mol/L and an aqueous sodium hydroxide solution adjusted to 3 mol/L. The aqueous solutions were mixed with each other in a flow rate ratio of 200 cc/min (MgCl$_2$) to 100 cc/min (NaOH) in a micro-device at a room temperature of 20 to 25° C. to obtain a magnesium hydroxide slurry. The resulting slurry was purified by water washing until the salt concentration reaches 0.00% to obtain an aqueous dispersion of fine magnesium hydroxide particles without aggregation. To the resulting aqueous dispersion was added 3-aminopropyltrimethoxysilane in an amount of 10% by weight based on the magnesium hydroxide particles, and the resulting mixture was kept at a room temperature of 20 to 25° C. for 30 minutes with stirring to surface-treat the particles. Then, the aqueous dispersion was further heated at 120° C. for 2 hours with stirring, and dried. FIG. 5A shows a SEM image of magnesium hydroxide obtained in Example 3, and FIG. 5B shows particle size distribution data of the aqueous dispersion obtained in Example 3.

Example 4

Figure 6A:
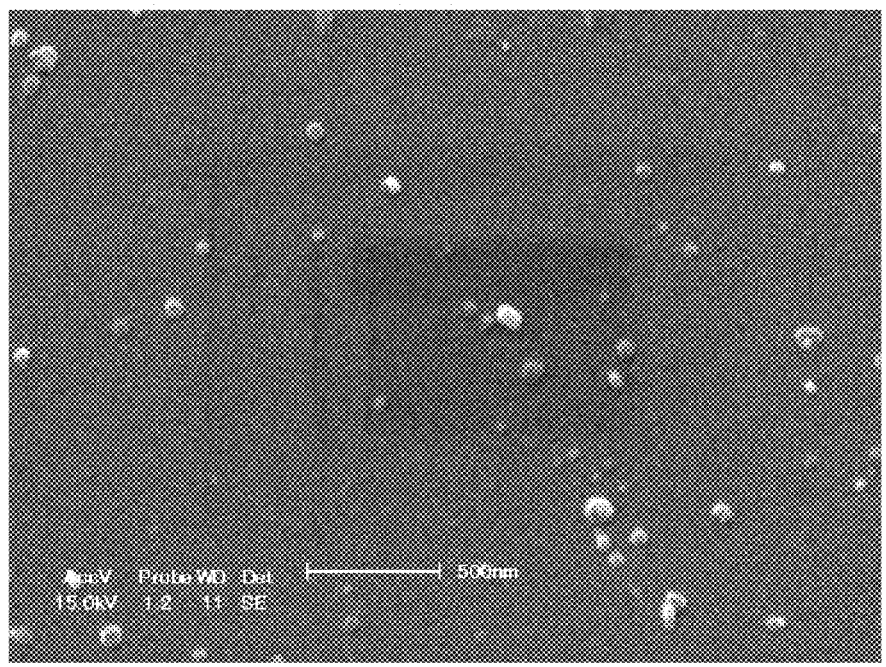
FIG. 6A shows a SEM image of magnesium hydroxide obtained in Example 4.
Figure 6B:
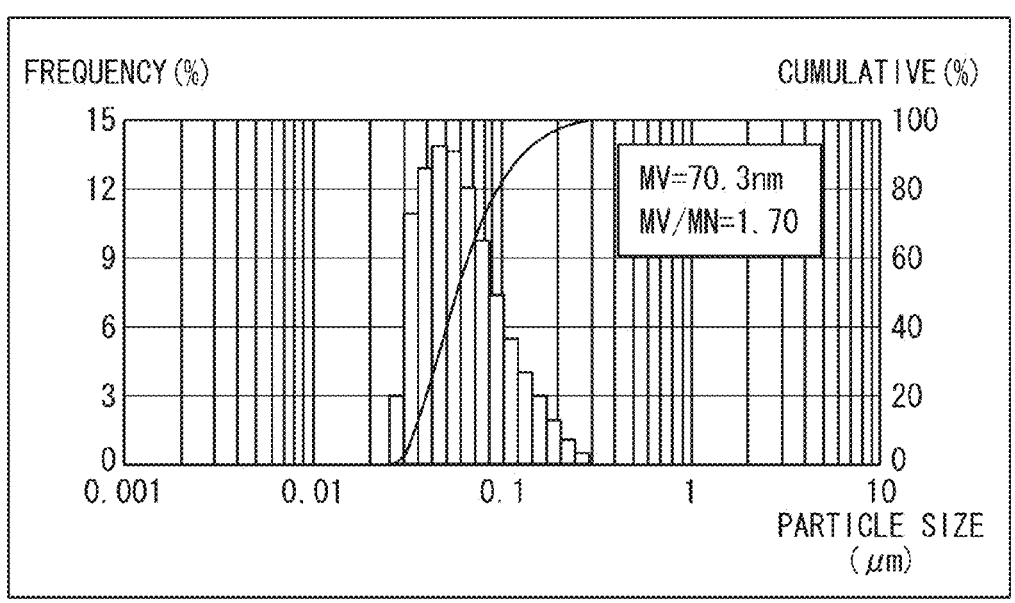
FIG. 6B shows particle size distribution data of the aqueous dispersion obtained in Example 4.

There were prepared an aqueous magnesium chloride solution adjusted to 0.5 mol/L and an aqueous sodium hydroxide solution adjusted to 3 mol/L. The aqueous solutions were mixed with each other in a flow rate ratio of 200 cc/min (MgCl$_2$) to 100 cc/min (NaOH) in a micro-device at a room temperature of 20 to 25° C. to obtain a magnesium hydroxide slurry. The resulting slurry was purified by water washing until the salt concentration reaches 0.00% to obtain an aqueous dispersion of fine magnesium hydroxide particles without aggregation. To the resulting aqueous dispersion was added 3-aminopropyltrimethoxysilane in an amount of 1% by weight based on the magnesium hydroxide particles, and the resulting mixture was kept at a room temperature of 20 to 25° C. for 30 minutes with stirring to surface-treat the particles. Then, the aqueous dispersion was further heated at 120° C. for 2 hours with stirring, and dried. FIG. 6A shows a SEM image of magnesium hydroxide obtained in Example 4, and FIG. 6B shows particle size distribution data of the aqueous dispersion obtained in Example 4.

Example 5

Figure 7A:
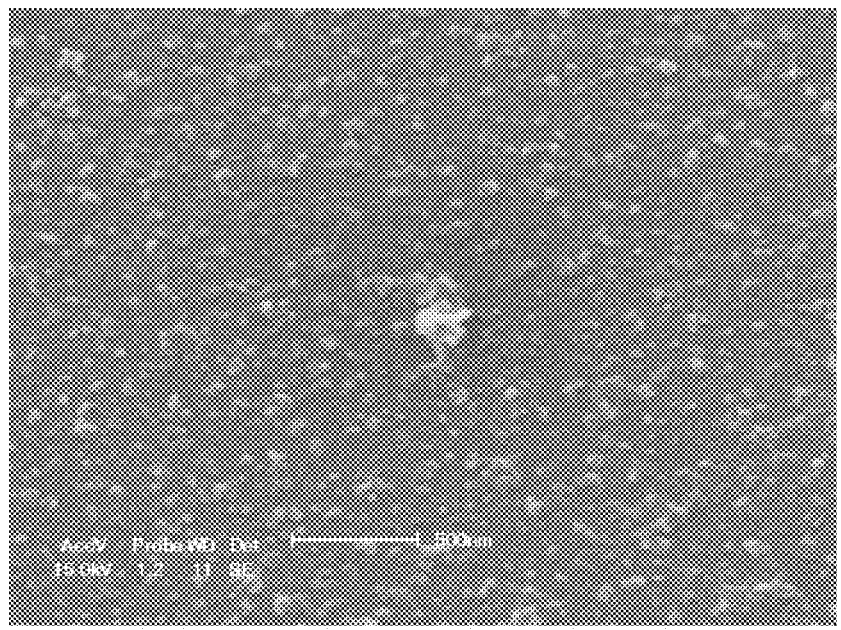
FIG. 7A shows a SEM image of magnesium hydroxide obtained in Example 5.
Figure 7B:
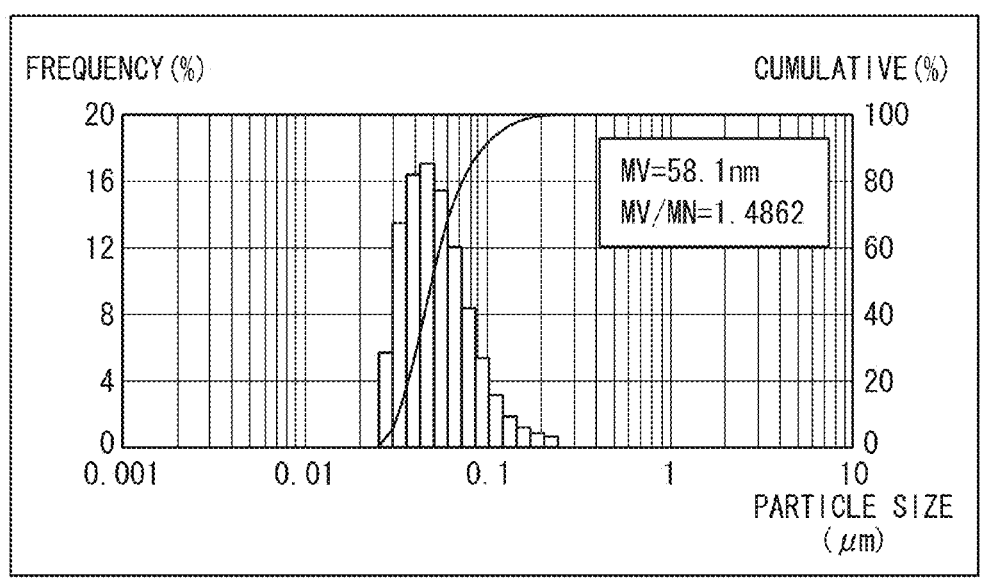
FIG. 7B shows particle size distribution data of the aqueous dispersion obtained in Example 5.

There were prepared 200 cc of an aqueous magnesium chloride solution adjusted to 0.5 mol/L and 100 cc of an aqueous sodium hydroxide solution adjusted to 3 mol/L. Into the aqueous magnesium chloride solution stirred in a beaker was dropped the aqueous sodium hydroxide solution through a nozzle having an inner diameter of 0.8 mm at a rate of 100 cc/min at a room temperature of 20 to 25° C. to obtain a magnesium hydroxide slurry. The resulting slurry was purified by water washing until the salt concentration reaches 0.00% to obtain an aqueous dispersion of fine magnesium hydroxide particles without aggregation. To the resulting aqueous dispersion was added 3-aminopropyltrimethoxysilane in an amount of 10% by weight based on the magnesium hydroxide particles, and the resulting mixture was kept at a room temperature of 20 to 25° C. for 30 minutes with stirring to surface-treat the particles. Then, the aqueous dispersion was further heated at 120° C. for 2 hours with stirring, and dried. FIG. 7A shows a SEM image of magnesium hydroxide obtained in Example 5, and FIG. 7B shows particle size distribution data of the aqueous dispersion obtained in Example 5.

Comparative Example 1

Figure 8A:
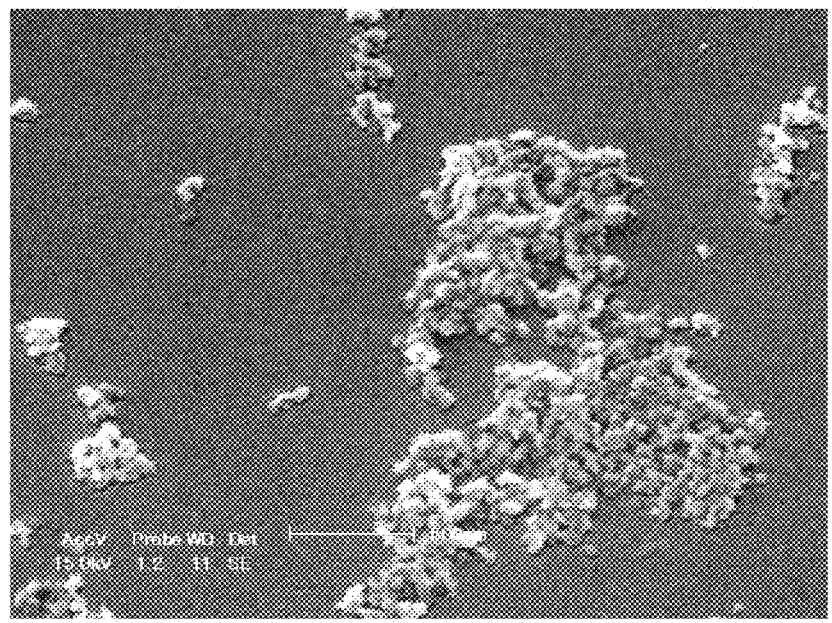
FIG. 8A shows a SEM image of magnesium hydroxide obtained in Comparative Example 1.
Figure 8B:
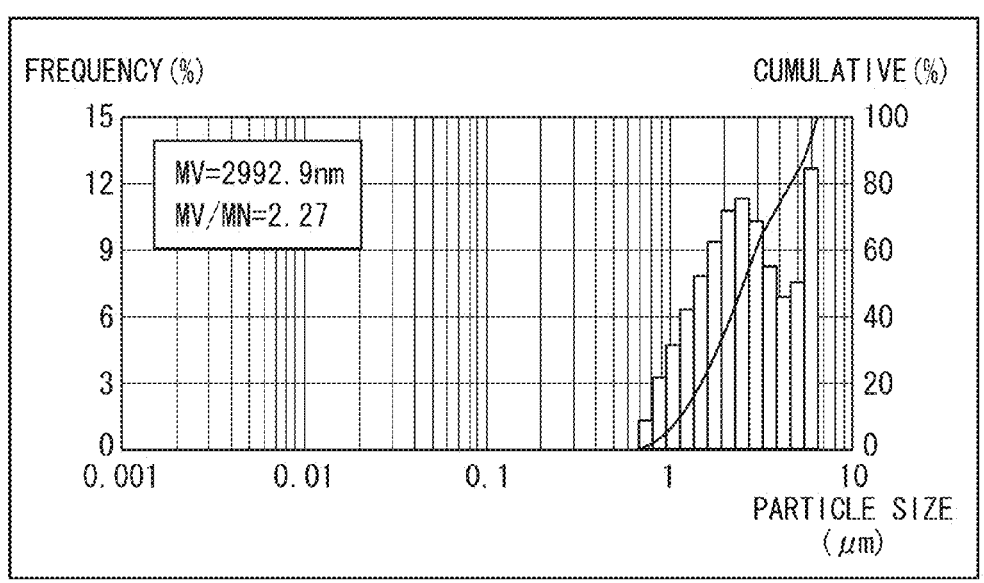
FIG. 8B shows particle size distribution data of the aqueous dispersion obtained in Comparative Example 1.

There were prepared an aqueous magnesium chloride solution adjusted to 0.5 mol/L and an aqueous sodium hydroxide solution adjusted to 3 mol/L. The aqueous solutions were mixed with each other in a flow rate ratio of 200 cc/min (MgCl$_2$) to 100 cc/min (NaOH) in a micro-device at a room temperature of 20 to 25° C. to obtain a magnesium hydroxide slurry. The resulting slurry was heated at 120° C. for 2 hours. Then, the slurry was purified by water washing until the salt concentration reached 0.00%, and dried. FIG. 8A shows a SEM image of magnesium hydroxide obtained in Comparative Example 1, and FIG. 8B shows particle size distribution data of the aqueous dispersion obtained in Comparative Example 1.

Comparative Example 2

Figure 9A:
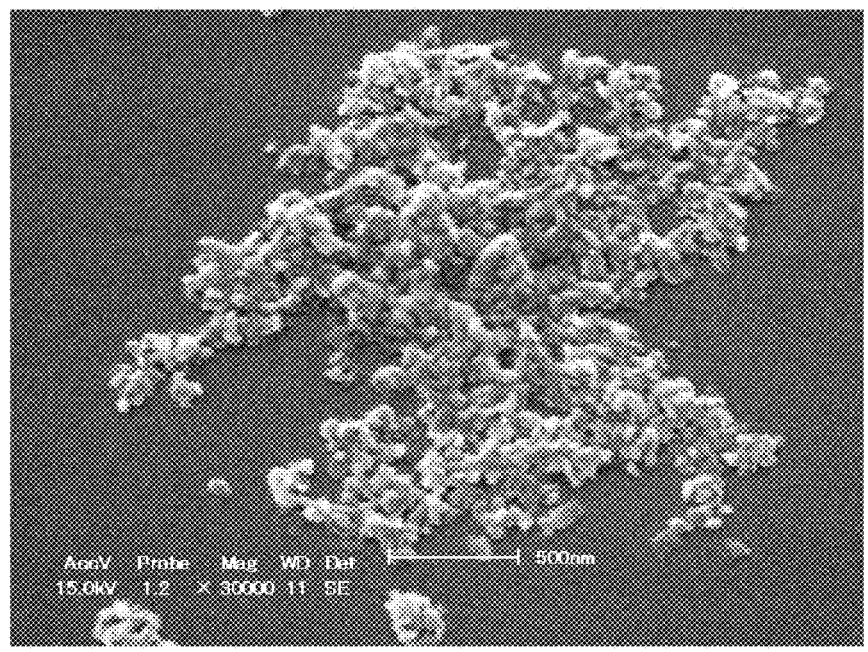
FIG. 9A shows a SEM image of magnesium hydroxide obtained in Comparative Example 2.
Figure 9B:
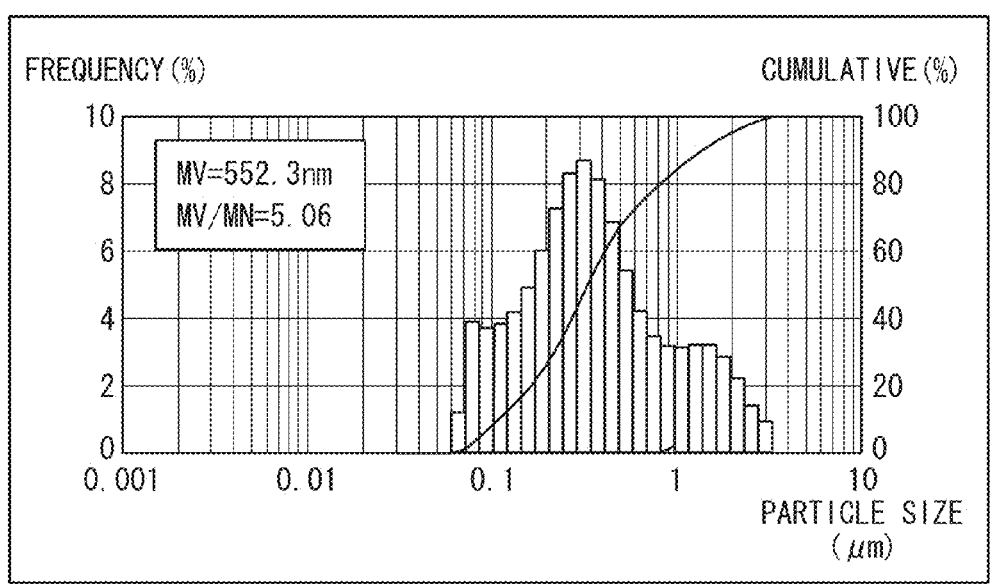
FIG. 9B shows particle size distribution data of the aqueous dispersion obtained in Comparative Example 2.

There were prepared an aqueous magnesium chloride solution adjusted to 0.5 mol/L and an aqueous sodium hydroxide solution adjusted to 3 mol/L. The aqueous solutions were mixed with each other in a flow rate ratio of 200 cc/min (MgCl$_2$) to 100 cc/min (NaOH) in a micro-device at a room temperature of 20 to 25° C. to obtain a magnesium hydroxide slurry. To the resulting slurry was added 3-aminopropyltrimethoxysilane in an amount of 10% by weight based on the magnesium hydroxide particles, and the resulting mixture was stirred for 30 minutes and further heated at 120° C. for 2 hours with stirring. The resulting slurry was purified by water washing until the salt concentration reached 0.00%, and dried. FIG. 9A shows a SEM image of magnesium hydroxide obtained in Comparative Example 2, and FIG. 9B shows particle size distribution data of the aqueous dispersion obtained in Comparative Example 2.

Comparative Example 3

Figure 10A:
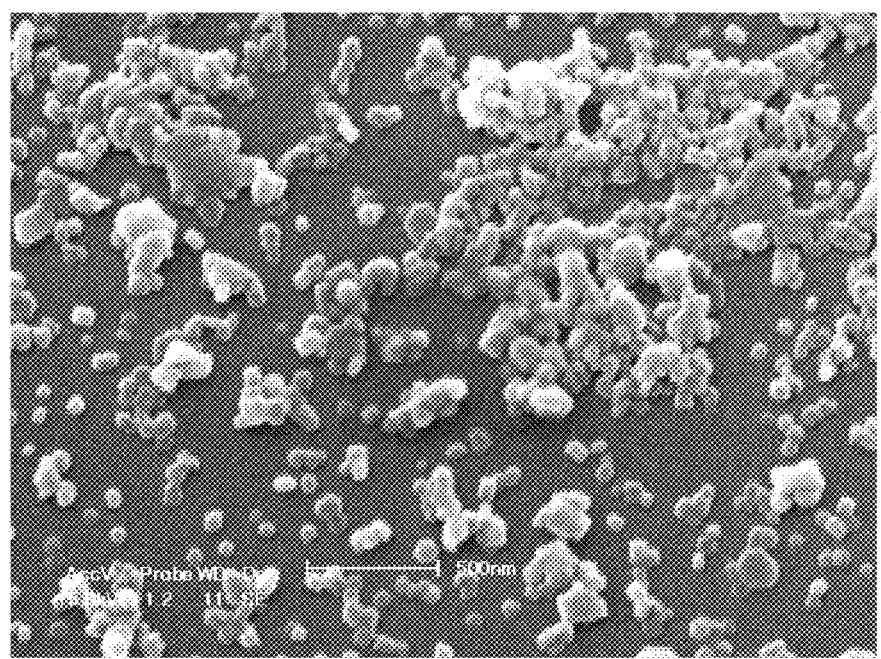
FIG. 10A shows a SEM image of magnesium hydroxide obtained in Comparative Example 3.
Figure 10B:
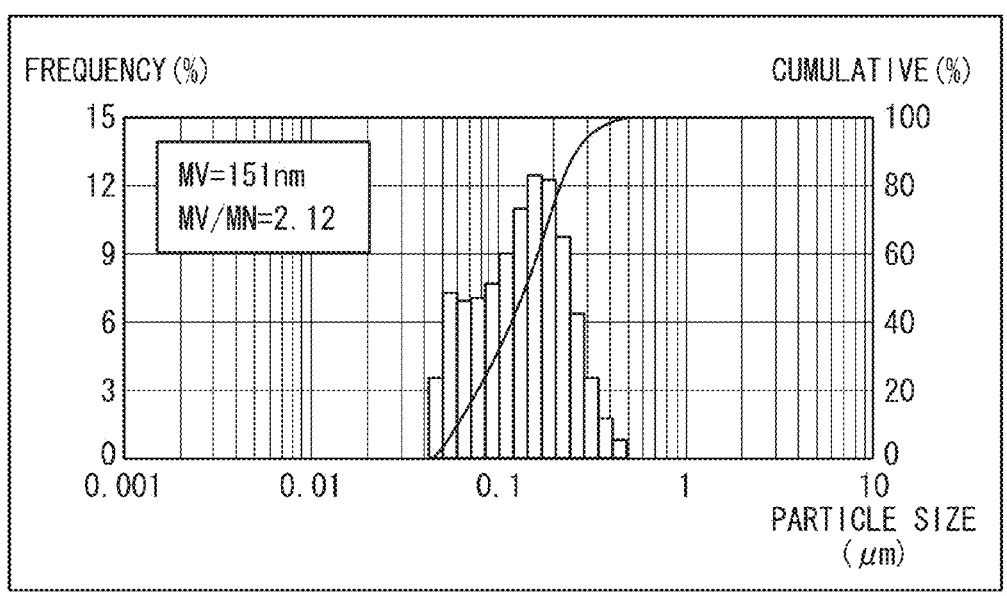
FIG. 10B shows particle size distribution data of the aqueous dispersion obtained in Comparative Example 3.

There were prepared 200 cc of an aqueous magnesium chloride solution adjusted to 0.5 mol/L and 100 cc of an aqueous sodium hydroxide solution adjusted to 3 mol/L. Into the aqueous magnesium chloride solution stirred in a beaker was dropped the aqueous sodium hydroxide solution through a nozzle having an inner diameter of 0.8 mm at a rate of 100 cc/min at a room temperature of 20 to 25° C. to obtain a magnesium hydroxide slurry. The resulting slurry was purified by water washing until the salt concentration reached 0.00% and then heated at 120° C. for 2 hours with stirring. To the resulting slurry was added 3-aminopropyltrimethoxysilane in an amount of 10% by weight based on the magnesium hydroxide particles, and the resulting mixture was stirred for 30 minutes and then dried. FIG. 10A shows a SEM image of magnesium hydroxide obtained in Comparative Example 3, and FIG. 10B shows particle size distribution data of the aqueous dispersion obtained in Comparative Example 3.

<Evaluation>

In Examples 1 to 5, the dispersions were extremely transparent because the particles were hardly aggregated, had very small particle sizes, and had a substantially monodisperse particle size distribution, as shown in FIGS. 3A to 7B.

On the other hand, in Comparative Examples 1 to 3, the dispersions were suspended because the particles were significantly aggregated to result in larger secondary particle sizes and a polydisperse particle size distribution, as shown in FIGS. 8A to 10B.

What is claimed is:

1. A method for producing fine metal hydroxide particles, comprising:
    a reaction step of mixing an aqueous solution of a metal salt with an aqueous solution of a hydroxide salt to precipitate metal hydroxide particles in an uncrystallized state;
    a purification step of removing by-product salt from a mixed solution containing the precipitated metal hydroxide particles in an uncrystallized state;
    a surface treatment step of treating a surface of the metal hydroxide particles in an uncrystallized state obtained through the purification step with a surface-treatment agent; and
    a heating step of crystallizing the surface-treated metal hydroxide particles in an uncrystallized state by hydrothermal treatment.

2. The method for producing fine metal hydroxide particles according to claim 1, wherein the metal salt is a magnesium salt.

3. The method for producing fine metal hydroxide particles according to claim 1, wherein the concentration of the by-product salt after the purification step is 0.05% or less, preferably 0.01% or less.

4. The method for producing fine metal hydroxide particles according to claim 2, wherein the concentration of the by-product salt after the purification step is 0.05% or less, preferably 0.01% or less.

5. The method for producing fine metal hydroxide particles according to claim 1, wherein the reaction step comprises:
    supplying the aqueous solution of the metal salt through some of a plurality of supply channels of a microdevice having a plurality of supply channels for supplying two or more fluids, a junction joined to the plurality of supply channels, and a discharge channel connected to the junction;
    supplying the aqueous solution of the hydroxide salt through others of the plurality of supply channels;
    mixing the metal salt with the hydroxide salt in the junction; and
    discharging a mixed solution from the discharge channel.

6. The method for producing fine metal hydroxide particles according to claim 4, wherein the reaction step comprises:
    supplying the aqueous solution of the metal salt through some of a plurality of supply channels of a microdevice having a plurality of supply channels for supplying two or more fluids, a junction joined to the plurality of supply channels, and a discharge channel connected to the junction;
    supplying the aqueous solution of the hydroxide salt through others of the plurality of supply channels;
    mixing the metal salt with the hydroxide salt in the junction; and
    discharging a mixed solution from the discharge channel.

7. The method for producing fine metal hydroxide particles according to claim 1, wherein the surface-treatment agent is a silane coupling agent.

8. The method for producing fine metal hydroxide particles according to claim 6, wherein the surface-treatment agent is a silane coupling agent.

9. The method for producing fine metal hydroxide particles according to claim 7, wherein the silane coupling agent is in the range of 0.1 to 50% by weight based on the metal hydroxide particles, in the surface treatment step.

10. The method for producing fine metal hydroxide particles according to claim 8, wherein the silane coupling agent is in the range of 0.1 to 50% by weight based on the metal hydroxide particles, in the surface treatment step.

11. The method for producing fine metal hydroxide particles according to claim 1, wherein the heating step is further followed by a drying step.

12. The method for producing fine metal hydroxide particles according to claim 10, wherein the heating step is further followed by a drying step.

13. The method for producing fine metal hydroxide particles according to claim 1, wherein the crystallized metal hydroxide particles have a volume average particle size (MV) of 0.01 μm to 1 μm and a ratio (MV/MN) of the volume average particle size (MV) to the number average particle size (MN) of 2.0 or less.

14. The method for producing fine metal hydroxide particles according to claim 12, wherein the crystallized metal hydroxide particles have a volume average particle size (MV) of 0.01 μm to 1 μm and a ratio (MV/MN) of the volume average particle size (MV) to the number average particle size (MN) of 2.0 or less.

* * * * *